United States Patent

Cline

[11] Patent Number: 6,058,218
[45] Date of Patent: May 2, 2000

[54] ENHANCED VISUALIZATION OF WEAK IMAGE SOURCES IN THE VICINITY OF DOMINANT SOURCES

[75] Inventor: Harvey Ellis Cline, Schenectady, N.Y.

[73] Assignee: General Electric Company, Schenectady, N.Y.

[21] Appl. No.: 08/967,654

[22] Filed: Nov. 10, 1997

[51] Int. Cl.[7] .................................................. G06K 9/40
[52] U.S. Cl. .......................... 382/254; 382/128; 382/257; 382/270; 382/283
[58] Field of Search .................................. 382/128, 130, 382/254, 257, 270, 282, 283

[56] References Cited

U.S. PATENT DOCUMENTS 5,659,629  8/1997  Cline ........................................ 382/131

OTHER PUBLICATIONS

"Coronary Arteries: Three-dimensional MR Imaging with Respective Respiratory Gating" by. D. Li, S. Kaushikkar, E.M. Haacke et al., Radiology 201, 857–863 (1996).

"Fast Three Dimensional Magnetic Resonance Imaging" by P. Irarrazaval, D. G. Nishimmura, Magn. Reson. Med. 33, 656–662, (1995).

"Vascular Morphology by Three–dimensional Magnetic Resonance Imaging", Magnetic Resonance Imaging, by H.E. Cline, W.E. Lorensen, R.J. Herfkens, G.A. Johnson, G.H. Glover, vol. 7, pp. 45–54 (1989).

"Image Analysis and Mathematical Morphology" by J. Serra, Academic Press, New York, pp. 373–416, (1982).

Primary Examiner—Thomas D. Lee
Attorney, Agent, or Firm—Jean K. Testa; Marvin Snyder

[57] ABSTRACT

A volumetric data set having a high intensity, dominant structure, near smaller, less intense structures is smoothed and segmented to separate the dominant structure. The dominant structure is masked out to result in the smaller, less intense structures which are displayed. For example, dominant structures such as the blood pool in atria, ventricles, and the aorta of a 3D angiography data set is segmented and removed from the data set using mathematical morphology operations to result in an enhanced data set. The enhanced data set is displayed by conventional means such as a maximum intensity projection (MIP) at different views to yield images of coronary arteries.

12 Claims, 5 Drawing Sheets

ENHANCED VISUALIZATION OF WEAK IMAGE SOURCES IN THE VICINITY OF DOMINANT SOURCES

BACKGROUND OF THE INVENTION

1. Scope of the Invention

The present invention relates to three-dimensional (3D) imaging, and more specifically, 3D imaging of less intense structures near dominant structures.

2. Discussion of Prior Art

In many different types of imaging, a large, or intense source will dominate and hide weaker, less intense, or smaller sources. This may appear in different types of imaging. One specific type is medical imaging, and mores specifically cardiac imaging.

Coronary artery disease is the leading cause of death in the United States and a major contribution to health care costs. Despite recent advances in magnetic resonance (MR) cardiac imaging, and x-ray catheterization, coronary angiography is the definitive examination for coronary artery disease. Coronary arteries are examined on medical images from different viewpoints using contrast material injected with a catheter into either the right or left coronary while examined under fluoroscopic imaging. The coronary arteries are small, less intense sources, as compared with the blood pools of the atria, ventricles and aorta, which dominate coronary images. If coronary arteries could be more clearly imaged, coronary artery disease could be diagnosed by viewing the coronary artery tree. And more specifically if the images could be obtained with MR imaging, patients may not require painful catheterization.

Manual methods for removing the blood pool from an acquired medical image data set before display are described in "Coronary Arteries: Three-dimensional MR Imaging with Respective Respiratory Gating" by D Li, S Kaushikkar, E M Haacke et al, *Radiology* 201, 857–863 (1996). This requires tedious manual user interaction to trace the outline of the coronary arteries.

Other strategies for segmenting the coronary arteries may find vessels by connectivity or tracking the lumen. However, discontinuities in the vessels and noise connecting the vessels to the blood pool may defeat automatic vessel finding techniques.

Currently, there is s need for a system which automatically produces images of smaller, less intense structures in a region near a larger, dominant structures.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

SUMMARY OF THE INVENTION

The present invention is a system for creating enhanced images of desired structures near dominant structures.

A volumetric data set I having a dominant structures with weaker desired structures is compared to a threshold C which may be interactively user-supplied. A 3D binary data set X={I>C} is created with data values of data set I above the threshold being one bit value and the other bit value indicating values of I which are on or below the threshold. This would include both the dominant and desired structures with some noise.

3D binary data set X is smoothed to result in smoothed data set Y substantially eliminating the desired structures and reducing noise. One such method of smoothing is erosion using structural elements receives $B_0$ having a radius $r_0$ to result in an eroded data set ($X \ominus B_0$). Then dilation of the eroded data set ($X \ominus B_0$) with structural element $B_1$ having radius $r_1$, to result in smoothed data set Y substantially excluding desired structures and having reduced noise.

A 3D mask M is created by dilating the smoothed data set Y with a structuring element $B_2$ to result in a dilated data set ($B_2$ ($B_2 \oplus Y$). The smoothed data set Y is then subtracted from the dilated data set ($B_2 \oplus Y$) to result in mask $M=(B_2 \oplus Y)-Y$.

Mask M is intersected with the original data set I to result in an enhanced data set E including the desired structures and omitting the dominant blood pool, $E=M \cap I$.

This enhanced data set E may then be manipulated and displayed by conventional imaging techniques such as maximum intensity projection (MIP) to result in a enhanced images.

In an alternative embodiment a user may interactively select locations on a displayed image indicating desired structures. These locations are used as 'seeds' within the enhanced data set E. Locations within enhanced data set values E having substantially the same values as the 'seeds', indicating the same source type, and are physically connected to the 'seeds' either directly, or through the same source type are grouped together as a solid structure which may be removed or displayed separately from other locations.

The present invention may be employed in creating enhanced displays of tortuous coronary arteries in high resolution 3D MR images.

This may be performed to display coronary arteries of a subject using mathematical morphology to select a shell containing the coronary arteries and exclude the dominant blood pools. The 3D data is then projected from different views to construct angiograms that are in a familiar form for diagnosis by cardiologists.

OBJECTS OF THE INVENTION

It is an object of the present invention to provide a method of visualizing smaller, less intense structures which are near a large, dominant structure.

It is another object of the present invention to provide a system which automatically produces images of coronary vessels of a subject from a volumetric data set.

DETAILED DESCRIPTION OF THE INVENTION

The challenge is to remove large, intense signal sources in a volumetric which dominate and obscure nearby smaller, less intense signal sources which are desired to be imaged. In terms of cardiac imaging, the blood pools of the atria, ventricles, and aorta dominate an angiographic image such that the cardiac arteries are obscured. The coronary arteries supply blood to cardiac muscle. Visualization of these cardiac arteries is key in diagnosis and prevention of serious coronary disease.

Since these arteries are very tortuous, simple 2D plane images rarely provide adequate conceptualization of the arteries.

The present invention automatically removes the dominant blood pool sources from the 3D MR cardiac images to display the segmented blood vessels as interactive 3D structures which may be viewed from different viewpoints.

This results in an enhanced 3D data set which facilitates conventional imaging methods, such as maximum intensity projection (MIP) which commonly used in MR angiography. The MIP projection through 3D volume appears similar to a conventional cardiac X-ray.

Data Acquisition

A volumetric data set is acquired. One type of data compatible with the present invention is 3D MR data set for cardiac imaging as described in P. Irarrazaval. D. G. Nishimmura, "Fast Three Dimensional Magnetic Resonance Imaging", *Magn. Reson. Med.* 33, 689–696 (1995).

Coil Sensitivity Correction

If MR volumetric data is used, and it was acquired using a surface receive coil, coil sensitivity correction is required to adjust for the variable sensitivity of the surface coil regarding distance from the coil, i.e. sources closer to the coil or directly in front of the coil, produce a larger MR response signal, while those further from the coil, or off to a side of the coil produce a smaller MR response signal in the coil. This is described in U.S. Pat. No. 5,659,629 Aug. 19, 1997 by H. E. Cline.

Thresholding to Segment Pool

The present invention requires a 3D volumetric data set. One specifically important use is in identifying and displaying coronary arteries in a 3D volumetric data set. The present invention avoids the tedious step of manually outlining vessels and identifying the blood pool, by automatically smoothing the data set, and thresholding with user input.

A threshold is interactively set by a user operating a user interface interactively setting a threshold, which provides a white and black contrast of regions above/below the threshold. The user adjusts the threshold until the blood pool is clearly delineated. In an optional, alternative embodiment, a more sophisticated blood pool surface detector than simple thresholding may not require a coil sensitivity correction.

Isolating Blood Pool—Smoothing

The blood pool is separated from the coronary arteries by mathematical morphology operations of erosion and dilation as described in "Vascular Morphology by Three-dimensional Magnetic Resonance Imaging" by H E Cline, W E Lorensen, R J Herfkens, G A Johnson, G H Glover *Magn. Reson. Imaging* vol. 7, pp. 45–54, 1989.

Figure 1:
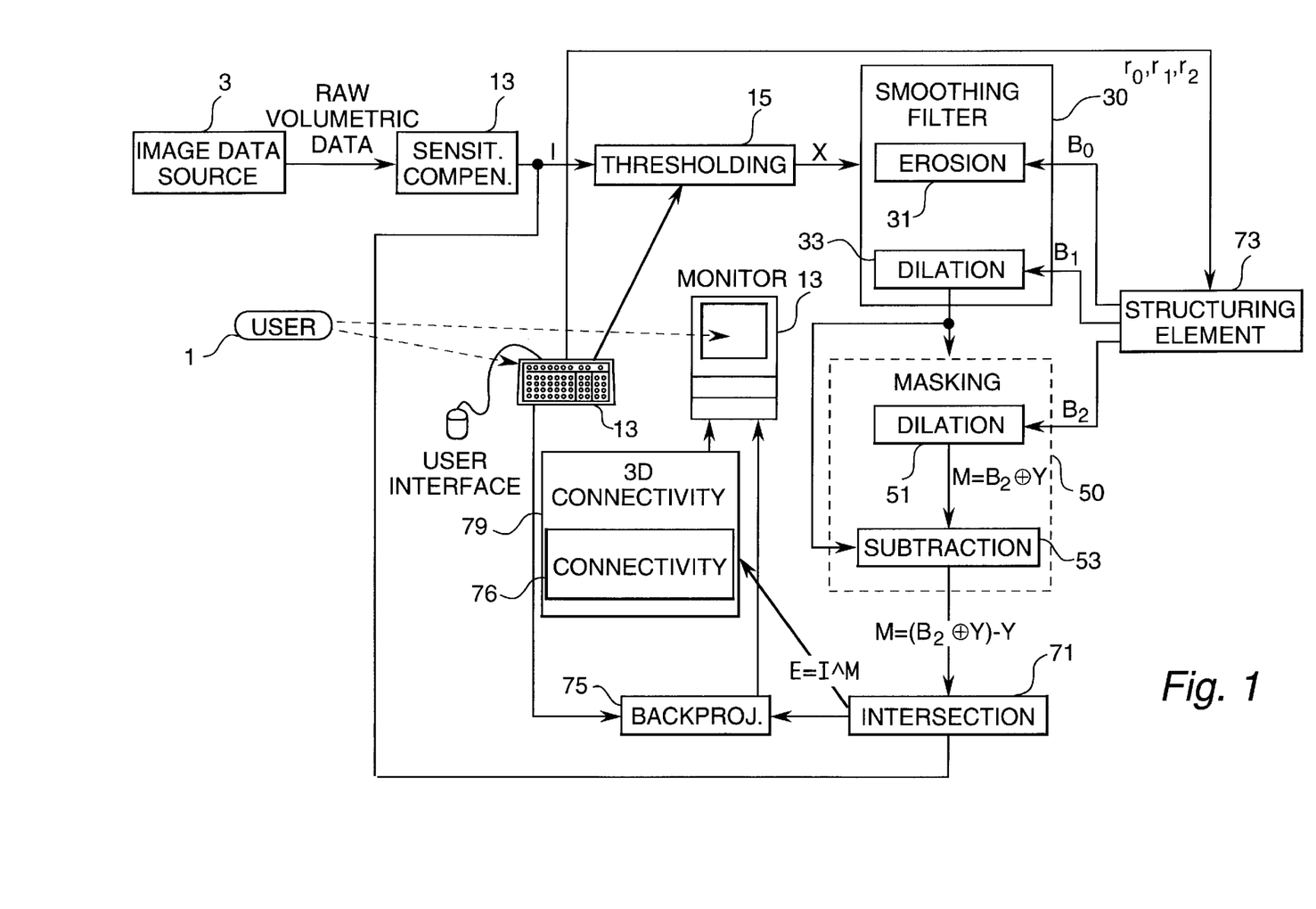
FIG. 1 is an illustration of a simplified block diagram of one embodiment of the present invention.

Erosion of a 3D object involves removing a surface region a given distance from the surface. In the case of isotropic data the structuring element approximates a sphere. A schematic of a blood pool with a coronary artery and noise is eroded as shown in FIG. 1. The noise and vessel are removed and the blood pool becomes smaller.

Dilation increases the size of an object and is equivalent to an erosion of the background. The combined erosion followed by a dilation, called an opening, removes small regions and smoothes a 3D binary object.

Mask Creation

Segmentation of the coronary arteries involves a dilation of the smoothed blood pool Y with a structural element B2 having a radius $r_2$ predefined or user-selected. This result in a dilated blood pool $(Y \oplus B_2)$ The original smoothed blood pool Y is subtracted from the dilated blood pool $(Y \oplus B_2)$ to form a 3D shell mask region $M=(Y \oplus B_2)-Y$ outside the blood pool that contains the arteries of interest. Mask M then includes the coronary arteries and substantially excludes the blood pools.

Creation of Enhanced Data Set E

Mask M is then intersected ∩ with compensated data set I form the enhanced data set E. Wherever mask M is '0', the enhanced data set E entry is '0'; and wherever mask M is '1', the enhanced data set E entry is set to the corresponding entry in the compensated data set I.

Display of Enhanced Data Set E

The processed 3D data set may be interactively manipulated to select parameters for segmentation and to visualize the coronary vessels. MIP of the coronary angiogram is a rapid means of display that dramatically improves depth perception especially if the images are rotated from different viewpoints.

In an alternative embodiment, displacement of the subject due to respiration is stored, and the 2D images created may be distorted by this amount to compensate for respiratory displacements preventing artificial discontinuities in the coronary arteries.

The steps to segment the blood pool and create MR coronary angiograms is as follows:

1. A raw 3D volumetric data set is corrected for local coil sensitivity resulting in a compensated data set I.
2. Compensated data set I is transformed by thresholding with a constant value C to create a 3D binary image X of the of the blood contained in both the blood pool and coronary arteries, $X=\{I>C\}$.
3. A smoothed data volume Y is created by erosion/dilation using structural elements receives $B_0$, $B_1$ having radii $r_0$, $r_1$, respectively. Smoothed blood pool Y does not include coronary arteries and has reduced noise. In this case, the set of points within a selected radius defines the structuring elements $B_0$, and $B_1$.

4. A mask $M=(Y \oplus B_2)-Y$ encompassing the coronary arteries is created by dilating the smoothed blood pool Y with a larger structuring element $B_2$ and subtracting the original blood pool Y.
5. Mask M is intersected ∩ with compensated data set I to form the enhanced data set E.
6. Enhanced data set E may then be displayed by conventional techniques, such as MIP, $\pi$, to form a coronary angiogram A. The view may be rotated by projecting from different viewpoints to create a moving representation of the coronary vessel tree, $A=\pi(I \cap M)$.

FIG. 1 shows a simplified block diagram of the present invention. An image data source provides raw volumetric data which covers a region intended to be visualized. This raw volumetric data, if acquired using a surface coil, is compensated for the sensitivity of the coil by a sensitivity compensation device 13 similar to that described in Cline (ibid.), to result in compensated data set I, and is provided to a thresholding device 15.

In an alternative embodiment, the volumetric data may be acquired by a coil which requires no compensation, or has been precompensated and is provided directly to thresholding device 15.

Thresholding device 15 also receives a threshold, which may be interactively set by a user 1 interacting with a user interface 11. Thresholding device 15 compares each of the data values of the compensated volumetric data set I to the threshold received and creates a volumetric data set X which has a value of '1' where each of the values exceeds the threshold and a value of '0' where each of the values of I fall at or below the threshold.

Volumetric data set X is then displayed on a monitor 17 to user 11 such that user 1 may interact with thresholding device 15 through user interface 11 to adjust the threshold such that the desired portions of volume of compensated data set I be excluded. If the data set used is a cardiac image, the threshold is adjusted such that the blood pools of the atria, ventricles and aorta are well-defined.

The thresholded data set X is provided to a smoothing filter 30 which smoothes the dominant source interactively selected by the user. Smoothing filter 30 reduces the noise around the dominant source and smoothes the edges of the dominant source.

One such smoothing filter would employ an erosion device 31 and a dilation device 33.

Erosion device 31 functions in coordination with structuring element device 73. User 1, through user interface 11, defines a radius $r_0$ corresponds to a region to be taken off of a dominant source 27. Radius $r_0$ defines a region in which volume pixels ('voxels') within that region are to be used. A set of voxels within that region is defined as a structuring element, and in this case is $B_0$. Each structuring element has a center voxel which will be modified based on testing the other voxels within the region.

Figure 2:
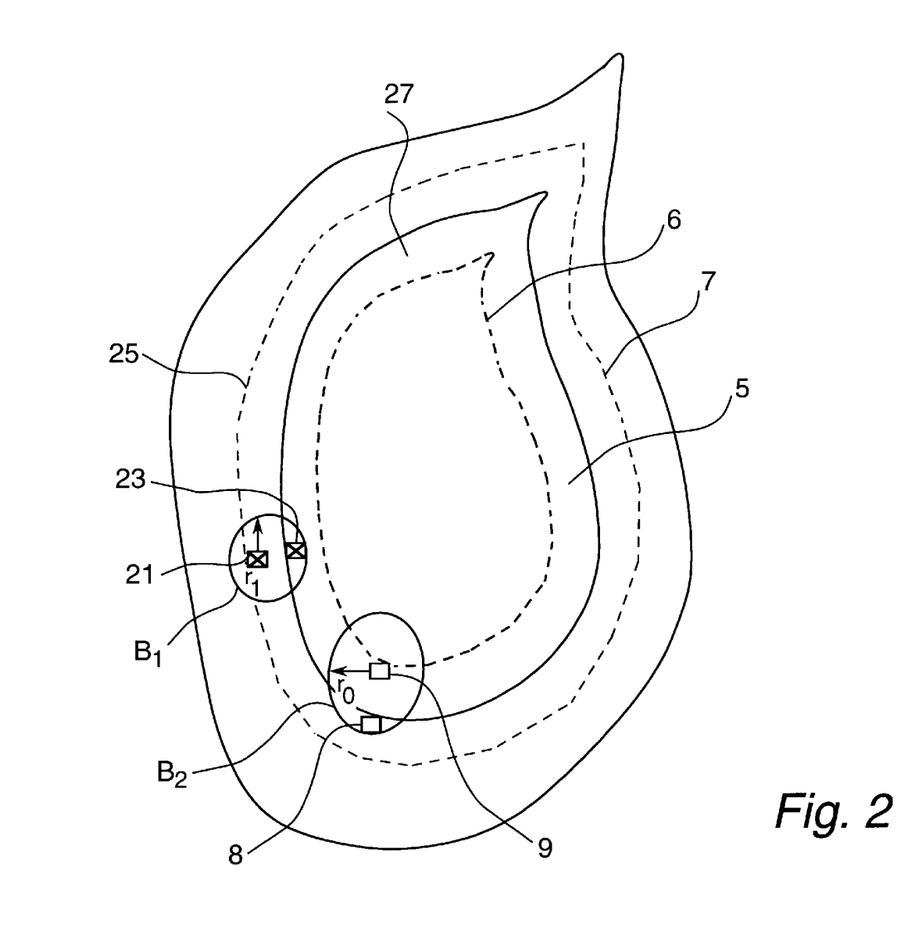
FIG. 2 is an illustration of a cardiac blood pool used in describing processes of erosion and dilation according to the present invention.

For example, with reference to FIG. 2, a voxel 8 is outside of a dominant source 27. Therefore in an erosion process, voxel 9, the center voxel, will be set to zero, in an erosion of a binary data set. Structuring element $B_0$ is then moved to another location and again a test is made to determine if any of the voxels are outside of the dominant source 27. If so, the center voxel is set to zero. This process continues until each voxel of a region of interest has been the center voxel. The result is a region shown by dashed line 6 becoming the new outer region of the eroded dominant source.

In FIG. 1, user 1 selects a radius $r_0$ through user interface 11 which is provided to structuring element device 73. This produces a structuring element $B_0$ which is provided to erosion device 31. Erosion device 31 then erodes the thresholded data volume X. The eroded volume is now known as $(B_0 \ominus X)$. This eroded volume is then passed to a dilation device 33.

In FIG. 2, a structuring element $B_1$ and voxels 21 and 23 are used to show dilation. A radius $r_1$ is chosen in which to dilate the volume. If dominant source 27 is to be dilated, all voxels within a radius $r_1$ of center voxel 21 are checked to see if any of these voxels are inside of dominant source 27. If at least one is, voxel 21 is set to a 1. Structuring element $B_1$ is then moved to a new location and the process continues. This is repeated until all voxels in the desired region have been the center voxel. This results in an enlargement to the dashed line shown as 25.

In the smoothing filter 30, the dominant source has been eroded first to dashed line 6 and then expanded again. If radius $r_0 = r_1$ it results in a dominant source having the same size as previously, but with a smooth surface and less noise. The process of erosion followed by dilation tends to erase small sources and random noise. The smooth data set is referred to as Y.

The smoothed data set Y is provided to a masking device 50 which creates a mask M that only includes desired peripheral structures and omits the dominant source. One such way of constructing mask M is to use the dilation device 51 employing a structural element $B_2$ which receives the smooth data set Y and creates a dilated data set $(B_2 \oplus Y)$.

A subtraction device 53 receives the output of the dilation device 51 and also receives the smooth data set Y and subtracts them to produce a mask $M=(B_2 \oplus Y)-Y$.

Figure 3A:
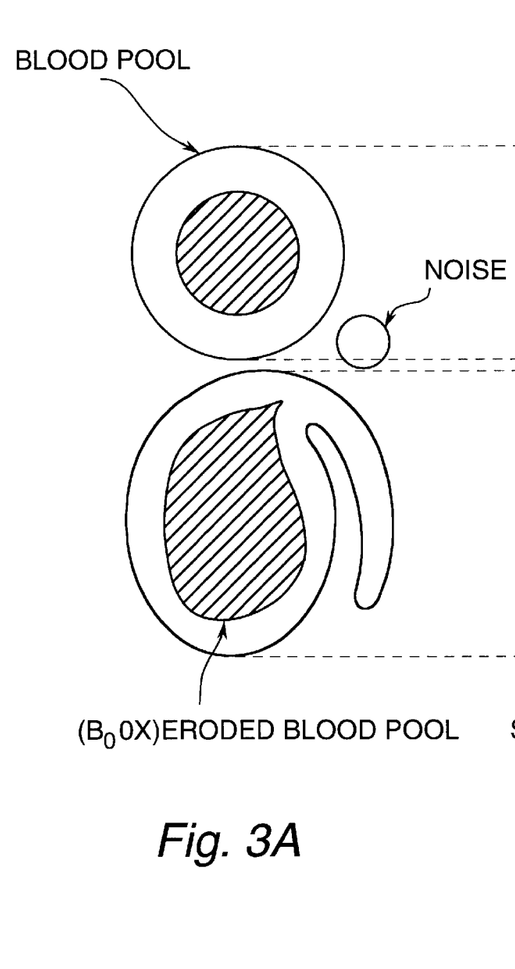
FIG. 3 is an illustration of the result of the steps in producing a mask M to augment visualization of coronary arteries according to one embodiment of the present invention.
Figure 3B:
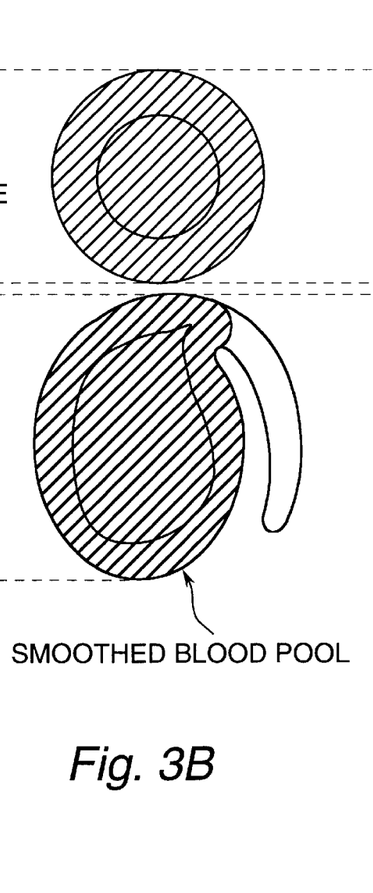
Figure 3C:
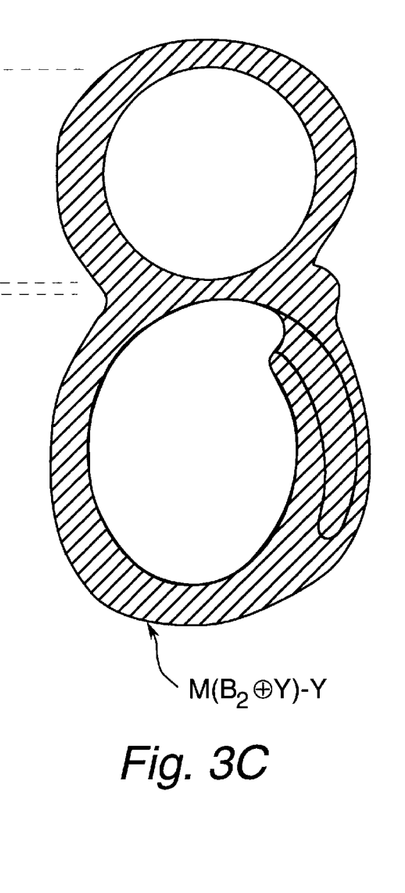

FIG. 3 shows the result of these operations. In FIG. 3, section A, the blood pool is shown after the erosion step $(B_0 \ominus X)$. This would be the output of erosion device 31.

In section B of FIG. 3, the smoothed blood pool Y is shown.

Smoothed blood pool Y is dilated by dilation device 51 and then the original smoothed blood pool Y is subtracted from the output of dilation device 51 by subtraction device 53 to produce the mask M as seen in FIG. 3, section C.

An intersection device 71, receives the output of subtraction device 53 and also receives the original compensated data set I and sets all values to zero except those which mask M has set to a value 1. This results in an enhanced data set E having the dominant sources removed. Enhanced data set E for a cardiac image resembles a 3D shell with the center removed. The shell has the coronary arteries which may be displayed.

Enhanced data set E may be manipulated by a three-dimensional (3D) workstation 79 or back projected by a back projection device 75 to produce images on monitor 17. User 1 may interact through user interface 11 to set the imaging parameters for 3D workstation 79 or back projection device 75. This shell may be back projected as it is, or may be cut up and back projected such that a clearer image is provided. For example, if the coronary artery desired to be imaged is on the anterior side of the heart, only the anterior portion of the heart near the artery may be used in back projection with the remainder of the shell omitted. This allows back projection without arteries on the posterior wall of the heart being overlapped on the anterior arteries, thereby confusing the image.

Another method of displaying these the enhanced data set E is to allow the user 1 to select a series of sequential viewpoints from which to view the images. These viewpoints may then be used to create images which are stored. The images may then be played back in a consecutively in a sequential fashion to produce a movie-like playback showing the structures as if the user were moving around the structures.

In an alternative embodiment, 3D workstation 79 may also perform the functions of thresholding device 15 and these devices be merged into a single device.

In another alternative embodiment, user 1 views the image on monitor 13. User 1 then selects locations, or 'seeds', within structures desired to be hilighted, such as coronary arteries through the use of user interface 11.

A connectivity device 76 within the 3D workstation 79 receives the 'seeds' as input, and searches for similar data values as the 'seed' values in the nearby vicinity, which are physically connected to the 'seeds': This may function as described in "Image Analysis and Mathematical Morphology" by J. Serra, Academic Press, New York, (1982), pp. 373–416. This result in solid structures of the same tissue type. When connectivity device 76 is used in connection with the system described above, further clarification of desired structures results.

Results

Figure 4:
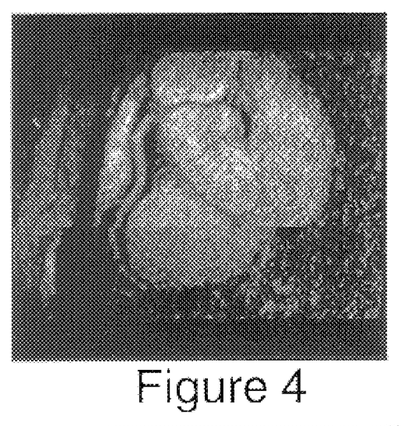
FIG. 4 shows a reformatted oblique slice through a conventional coronary blood.

FIG. 4 shows a reformatted oblique slice through the 3D volume at the right coronary artery (RCA) of a volumetric data set including coronary blood pools. Reformatted views were calculated interactively with the GE Research Workstation program Medic++ running on a workstation (Pentium Pro 200 MHz, Hewlett Packard). A user selects the angle, elevation or cut depth defining the oblique plane and the reformatted oblique images appear on the screen continuously in real-time.

After segmenting the 3D data set, the blood pools are automatically removed by the present invention resulting in an enhanced data set E.

Figure 5:
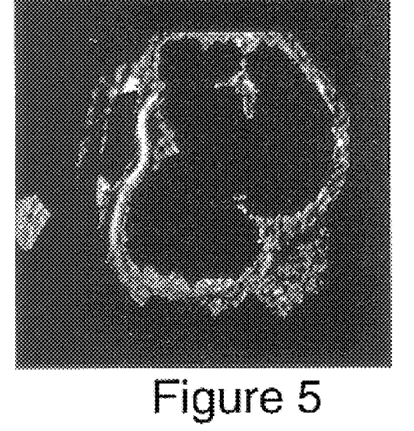
FIG. 5 is 2D slice of an enhanced data set E constructed in accordance with the present invention, from the same view as FIG. 4.

A slice through the 3D enhanced data set E is shown in FIG. 5. A structuring element of 3 mm radius was used to open and smooth the blood pool followed by a 7 mm dilation to create the shell mask M. The blood pool now appears black and does not obscure an MIP image.

Figure 6:
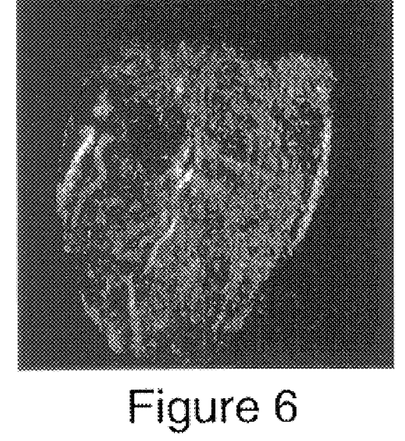
FIG. 6 is a projection through the enhanced data set E according to the present invention.

FIG. 6 is a projection through the enhanced data set E showing the left anterior descending artery (LAD) artery in the center of the image. A right transverse view of a subject's heart was used to visualize the left anterior descending (LAD) artery. Notice the LAD is non-planar and may not be simply displayed in a single planar image.

Figure 7:
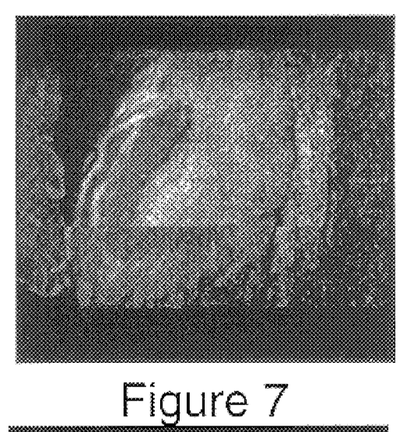
FIG. 7 is a conventional maximum intensity projection (MIP) image created from the original compensated data set I.

A stack of 10 parallel reformatted slices of the volumetric data spaced 1 mm apart were displayed using MIP to combine different vessel segments in a thick reformatted view as shown in FIG. 7. This includes the blood pool of the atria, ventricles, and aorta.

Figure 8:
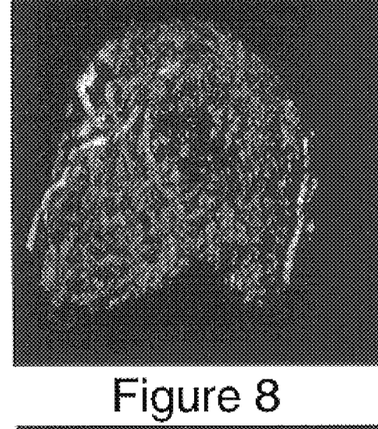
FIG. 8 is an MIP image from the same view as FIG. 7 starting with the same data set I but processed according to the present invention.

FIG. 8 is an MIP from the same view as FIG. 7 after the blood pool was segmented and masked out. This shows both the LAD and the left circumflex artery (LCX) which was obscured in FIG. 7.

Figure 9:
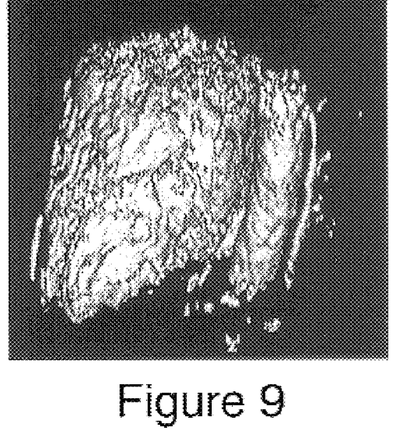
FIG. 9 is a 3D surface rendering at the same view as FIGS. 7 and 8.

FIG. 9 shows a 3D surface rendering at the same view as FIGS. 7 and 8. This shows the blood pool surface and LAD artery. Surfaces of the blood pool may be constructed and visualized with computer graphics conventional surface rendering routines. A 3D surface model is useful in determining the orientation of the epicardium. 3D surface models are created to specify the orientation of the view relative to features of the cardiac anatomy.

Figure 10:
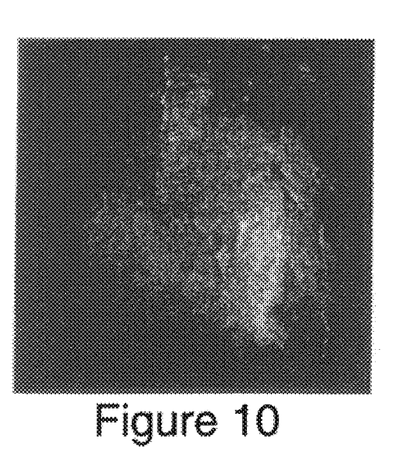
FIG. 10 is an MIP image of the original volumetric data set including the blood pool, according to conventional imaging techniques.

A left anterior oblique view at 49 degrees cranial was used. FIG. 10 is an MIP image of a 3D MR angiographic compensated data set I with the blood pool. The blood pool dominates the image and obscures the coronary arteries.

Figure 11:
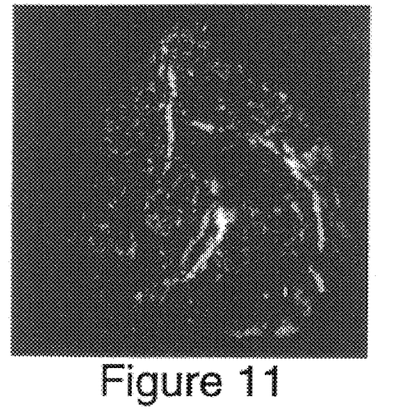
FIG. 11 is a segmented MIP image starting with the same data set, and having the same view as FIGS. 10 and 11 according to the present invention, showing coronary arteries.

FIG. 11 is a segmented MIP image of the same view as FIG. 10 showing the left coronary artery with some diagonal branches visible. This was is an MIP image from the enhanced data set E in which the blood pool was segmented and masked out before projection.

Figure 12:
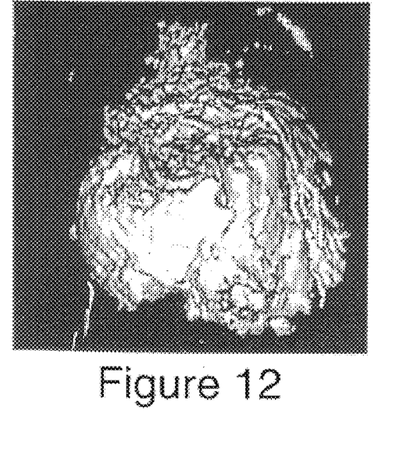
FIG. 12 is a 3D surface rendering of angiographic volumetric data set.

FIG. 12 is 3D surface rendering of the same original angiographic data set I of FIGS. 10 and 11, from the same view. The left coronary artery and right ventricle blood pool surfaces are visible.

Figure 13:
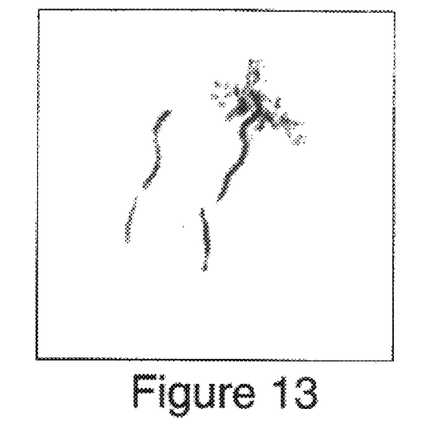
FIG. 13 is an MIP image of enhanced data set E which was further enhanced using connectivity, according to the present invention

FIG. 13 shows an MIP image of enhanced data set E which was further enhanced using connectivity as described above.

The present invention provides information beyond that obtained with both surface models and maximum intensity projections.

It provides visualization of the coronary angiogram as a rapid display that dramatically improves depth perception especially if the images are rotated from different viewpoints as in peripheral MR angiography presentations.

The present invention may be used as a complement to conventional reformatted sections superimposed upon original images from the same view to highlight coronary vessels.

While several presently preferred embodiments of the present novel invention have been described in detail herein, many modifications and variations will now become apparent to those skilled in the art. It is our intent therefore, to be limited only by the scope of the appending claims and not be the specific details and instrumentalities presented by way of explanation herein.

What we claim is:

1. A method of creating enhanced images of desired structures near dominant structures comprising the steps of:
   a) acquiring volumetric data set I having a dominant structures with weaker desired structures;
   b) applying a predetermined threshold C to the data set I to create a 3D binary data set X={I>C} of both dominant and desired structures also having some noise;
   c) smoothing 3D binary data set X to result in smoothed data set Y substantially eliminating the desired structures and reducing noise;
   d) creating a 3D mask M from the 3D binary data set X encompassing the desired structures but substantially excluding the dominant structure;
   e) intersecting mask M with the original data set I to result in an enhanced data set E including the desired structures and omitting the dominant structures, E=M∩I; and
   f) displaying the enhanced data set E by conventional imaging techniques to result in an enhanced image.

2. The method of creating enhanced images of claim 1 further comprising, before the step of displaying the enhanced data E, the steps of:
   a) receiving user-defined 'seeds' within desired structures of the enhanced data set E; and
   b) determining solid regions of enhanced data set values E having substantially the same values as the 'seeds', indicating the same source type, and are physically connected to the 'seeds' either directly, or through the same source type.

3. The method of creating enhanced images of claim 1 wherein the step of smoothing 3D binary data set X comprises the steps of:
   a) erosion using structural elements receives $B_0$ having a radius $r_0$ to result in an eroded data set $(X \ominus B_0)$;
   b) dilating the eroded data set $(X \ominus B_0)$ with structural element $B_1$ having radius $r_1$ to result in smoothed data set Y substantially excludes desired structures and has reduced noise.

4. The method of creating enhanced images of claim 1 wherein the step of creating a 3D mask M comprises the steps of:
   a) dilating the smoothed data set Y with a structuring element $B_2$ to result in a dilated data set ($B_2 \oplus Y$); and
   b) subtracting the smoothed data set Y from the dilated data set ($B_2 \oplus Y$) to result in mask $M=(B_2 \oplus Y)-Y$.

5. The method of creating enhanced images of claim 1 wherein the step of displaying the enhanced data set E comprises:
   performing maximum intensity projection (MIP), $\pi$, through enhanced data set E from a predetermined viewpoint to form an image $A=\pi(I \cap M)=\pi(E)$.

6. The method of creating enhanced images of claim 1 wherein the step of displaying the enhanced data set E comprises:
   a) performing a plurality of maximum intensity projections (MIP), $\pi$, through enhanced data set E from a plurality of consecutive viewpoints to form a plurality of images A;
   b) playing back the plurality of images A to simulate a movie of the desired structures as if a viewer were moving around the structures.

7. A method of creating enhanced coronary comprising the steps of:
   a) acquiring a volumetric angiographic data set I having a dominant blood pool source with coronary arteries being weaker sources surrounding the blood pool;
   b) applying a predetermined threshold C to the data set I to create a 3D binary data set $X=\{I>C\}$ both of the blood pool and coronary arteries also having some noise;
   c) smoothing 3D binary data set X to result in smoothed blood pool Y substantially eliminating the coronary arteries and reducing noise;
   d) creating a 3D mask M from the 3D binary data set X encompassing the coronary arteries but substantially excluding the blood pools;
   e) intersecting mask M with the original data set I to result in an enhanced data set E including the coronary arteries and omitting the dominant blood pool, $E=M \cap I$; and
   f) displaying the enhanced data set E by conventional imaging techniques to result in an enhanced image of the coronary arteries.

8. The method of creating enhanced images of claim 7 further comprising, before the step of displaying the enhanced data E, the steps of:
   a) receiving user-defined 'seeds' within coronary vessels of the enhanced data set E; and
   b) determining solid regions of enhanced data set values E having substantially the same values as the 'seeds', indicating the same tissue type, and are physically connected to the 'seeds' either directly, or through the same tissue type.

9. The method of creating enhanced images of claim 7 wherein the step of smoothing 3D binary data set X comprises the steps of:
   a) erosion using structural elements receives $B_0$ having a radius $r_0$ to result in an eroded data set ($X \ominus B_0$);
   b) dilating the eroded data set ($X \ominus B_0$) with structural element $B_1$ having radius $r_1$ to result in smoothed blood pool Y which does not include coronary arteries and has reduced noise.

10. The method of creating enhanced images of claim 7 wherein the step of creating a 3D mask M comprises the steps of:
    a) dilating the smoothed blood pool Y with a structuring element $B_2$ to result in a dilated blood pool ($B_2 \oplus Y$); and
    b) subtracting the smoothed blood pool Y from the dilated blood pool ($B_2 \oplus Y$) to result in mask $M=(B_2 \oplus Y)-Y$.

11. The method of creating enhanced images of claim 7 wherein the step of displaying the enhanced data set E comprises: performing maximum intensity projection (MIP), $\pi$, through enhanced data set E from a predetermined viewpoint to form a coronary angiogram $A=\pi(I \cap M)=\pi(E)$.

12. The method of creating enhanced images of claim 7 wherein the step of displaying the enhanced data set E comprises:
    a) performing a plurality of maximum intensity projections (MIP), $\pi$, through enhanced data set E from a plurality of consecutive viewpoints to form a plurality of coronary angiograms A;
    b) playing back the plurality of coronary angiograms A to simulate a movie of the coronary arteries as if a viewer were moving around the arteries.

* * * * *